United States Patent
Eyal et al.

(10) Patent No.: US 10,675,252 B2
(45) Date of Patent: Jun. 9, 2020

(54) VETERINARY COMPOSITION AND METHODS FOR PRODUCTION AND USE

(71) Applicant: Canna-B Cure Ltd, Or-Akiva (IL)

(72) Inventors: Aharon M. Eyal, Jerusalem (IL); Netta Lin-Cohen, Shilat (IL); Youval Lin, Kfar Billo (IL); Meir Ariel, Kazir (IL)

(73) Assignee: Canna-B Cure Ltd, Or-Akiva (IL)

( * ) Notice: Subject to any disclaimer, the term of this patent is extended or adjusted under 35 U.S.C. 154(b) by 44 days.

(21) Appl. No.: 15/781,384

(22) PCT Filed: Dec. 5, 2016

(86) PCT No.: PCT/IB2016/057368
§ 371 (c)(1),
(2) Date: Jun. 4, 2018

(87) PCT Pub. No.: WO2017/093986
PCT Pub. Date: Jun. 8, 2017

(65) Prior Publication Data
US 2018/0344662 A1    Dec. 6, 2018

Related U.S. Application Data

(60) Provisional application No. 62/263,617, filed on Dec. 5, 2015.

(51) Int. Cl.
*A61K 36/185*  (2006.01)
*A61K 31/05*   (2006.01)
*A61K 31/352*  (2006.01)
*A61K 45/06*   (2006.01)
*A61K 9/12*    (2006.01)
*A61K 47/26*   (2006.01)
*A61K 47/46*   (2006.01)

(52) U.S. Cl.
CPC .............. *A61K 31/05* (2013.01); *A61K 9/12* (2013.01); *A61K 31/352* (2013.01); *A61K 36/185* (2013.01); *A61K 45/06* (2013.01); *A61K 47/26* (2013.01); *A61K 47/46* (2013.01)

(58) Field of Classification Search
CPC .................................................... A61K 36/185
See application file for complete search history.

(56) References Cited

U.S. PATENT DOCUMENTS

| | | | |
|---|---|---|---|
| 7,431,938 B2 | 10/2008 | Roso et al. | |
| 9,186,386 B2 | 11/2015 | Speier | |
| 2009/0209499 A1 | 8/2009 | Orban | |
| 2010/0239693 A1* | 9/2010 | Guy | A61K 31/05 424/725 |
| 2013/0203692 A1 | 8/2013 | Soll et al. | |
| 2014/0302086 A1 | 10/2014 | Kelly | |
| 2015/0057342 A1 | 2/2015 | Dickman et al. | |

FOREIGN PATENT DOCUMENTS

| | | |
|---|---|---|
| CN | 105012684 | 11/2015 |
| ES | 2038081 | 7/1993 |
| RO | 122437 | 6/2009 |
| WO | 2008/120207 | 10/2008 |
| WO | 2009/013506 | 1/2009 |

OTHER PUBLICATIONS

Official Communication issued in International Bureau of WIPO Patent Application No. PCT/IB2016/057368, dated Jun. 5, 2018.
Official Communication issued in International Bureau of WIPO Patent Application No. PCT/IB2016/057368, dated Mar. 17, 2017.

* cited by examiner

*Primary Examiner* — Rosanne Kosson
(74) *Attorney, Agent, or Firm* — Eva Taksel

(57) ABSTRACT

Veterinary compositions and methods for production and use. A method of treating bees at or near a bee hive with a first and/or second veterinary composition is described including administering to bees a veterinary composition comprising at least cannabinoid, and/or at least two non-cannabinoid *cannabis* compounds, with or without a carrier, thereby enhancing bees performance.

13 Claims, No Drawings

VETERINARY COMPOSITION AND METHODS FOR PRODUCTION AND USE

CROSS-REFERENCE TO RELATED APPLICATIONS

The present application claims the benefit of U.S. Provisional Application Ser. No. 62/263,617 filed Dec. 5, 2015, the disclosure of which is expressly incorporated by reference herein in its entirety.

TECHNICAL FIELD

The field of art to which this invention generally pertains is veterinary compositions, and specifically treatment methods and compositions for bees.

BACKGROUND

The productivity of bees can be very sensitive to such things as viruses, stress, etc. This can show itself in many ways, such as, for example, amount of honey produced per a particular bee hive. Accordingly, there is a constant search in this area for ways to address these issues.

BRIEF SUMMARY

A method of treating bees at or near a bee hive with a veterinary first composition is described including administering to bees a veterinary first composition comprising at least one cannabinoid, and/or, at least two non-cannabinoid *cannabis* compounds, thereby enhancing bees performance.

Additional embodiments include: the method described above where said enhancing includes one or more of treating bees virus, treating bees inflammation, treating bees stress, treating bees against Colony Collapse Disorder, treating bees against *Varroa,* increasing the number of bee hive brood cells, including the number of bee hive sealed brood cells, improving bees pollination activity, strengthening bees immune system and improving bees honey production; the method described above where said veterinary composition comprises an extract of *cannabis* plant material; the method described above where said veterinary composition comprises tetrahydrocannabinol (THC) and/or cannabidiol (CBD); the method described above where said veterinary composition additionally contains an emulsifier and/or an antioxidant; the method described above where said veterinary composition includes at least one terpene; the method described above where said non-cannabinoid *cannabis* compounds comprise non-cannabinoid *cannabis* compounds characteristic to *Sativa cannabis* strains and/or to *Indica* strains; the method described above where said veterinary composition additionally contains an additive selected from the group consisting of sugars, pollen, pollen substitutes, pollen supplements, omega-3 fatty acids, vegetable oil, minerals, vitamins, fats, essential oils, invertase enzyme and combinations thereof; the method described above where said veterinary composition additionally contains an additive selected from the group consisting of compounds characteristic to *eucalyptus* flowers, compounds characteristic to avocado flowers, compounds characteristic to orange blossom, compounds characteristic to wild flowers, characteristic to *Tribulus terrestris* and combinations thereof; the method described above including administering said veterinary composition to the bees in combination with bees feed, or with bees feed additives or with both. The method of Claim 1, comprising administering said veterinary composition to the bees in combination with sugars; the method of claim 1 including administering said veterinary composition to the bees in combination with a protein ingredient; the method described above where said administering comprises vaporizing the composition in the beehive, spraying the composition into the atmosphere of the beehive, spraying the composition on honeycombs in the beehive, spraying the composition on brood-containing honeycombs, incorporating the composition into beeswax used to form the beehive frames or combination thereof; the method described above including administering said veterinary composition to the bees between 2 and 12 times per year; the method described above including administering said veterinary composition to the bees during winter; the method described above where said treating comprises administering to the bees between 1 milligram (mg) and 1000 milligram (mg) veterinary composition per beehive; the method of claim 1 including administering said veterinary composition to the bees when present at or near a beehive containing brood cells, wherein the count of brood cells in said beehive, the count of sealed brood cells in said beehive or both is at least 10% greater than those in a beehive under the same conditions receiving no veterinary composition treatment; the method described above where average size of said bees is at least 10% greater than that of bees under the same conditions receiving no veterinary composition treatment; the method of claim 1 where the bees contain *Varroa* and the average *Varroa* count in said bees is at least 10% lower than that of bees under the same conditions receiving no veterinary composition treatment.

A veterinary second composition particularly adapted for treatment of bees is also described including at least one cannabinoid and/or at least two non-cannabinoid *cannabis* compounds; a carrier; and optionally water where said at least one cannabinoid and/or said at least two non-cannabinoid *cannabis* compounds are homogeneously dispersed in said carrier; the composition includes a cannabinoid and the weight ratio between said carrier and said cannabinoid is greater than 5; the composition includes a cannabinoid and water and the weight ratio between the water and said cannabinoid is greater than 5; and/or the composition includes water and the weight ratio between said carrier and the water is greater than 0.5.

Additional embodiments include: the composition described above where said carrier comprises at least one of a sugar, honey, beeswax, pollen, pollen substitutes, and pollen supplements; the composition described above where said carrier comprises honey; the composition described above where the carrier comprises a sugar selected from the group consisting of sucrose, glucose, fructose and combinations thereof; the composition described above including at least 0.001% by weight cannabinoid, at least 0.001% by weight non-cannabinoid *cannabis* compounds and at least 40% by weight carrier; the composition described above where at least one cannabinoid and/or at least two non-cannabinoid *cannabis* compounds, at least 40% by weight sugar and at least 40% by weight water; the composition described above where at least one cannabinoid and/or at least two non-cannabinoid *cannabis* compounds and additionally containing pollen, pollen substitutes and/or pollen supplements; the composition described above where at least one cannabinoid and/or at least two non-cannabinoid *cannabis* compounds and additionally containing 30% protein; the composition described above additionally containing compounds characteristic to *eucalyptus* flowers, avocado flowers, orange blossom, wild flowers, *Tribulus terrestris* and/or combinations thereof; the composition described above additionally containing at least one terpene other than *cannabis* terpenes; the composition described above including non-cannabinoid *cannabis* compounds characteristic to *Sativa cannabis* strains and/or to *Indica* strains; the composition described above including tetrahydrocannabinol (THC) and/or cannabidiol (CBD); the composition described above including tetrahydrocannabinol and cannabidiol at weight/weight ratio between 1:10 and 10:1; the composition described above where at least one of said non-cannabinoid *cannabis* compounds is selected from the group consisting of terpenes and flavonoids; the composition described above additionally containing an emulsifier and/or an antioxidant; the composition described above additionally containing a pharmaceutical; the composition described above additionally containing an additive selected from the group consisting of omega-3 fatty acids, minerals, vitamins, fats, invertase enzyme, essential oils, and combinations thereof. A bee feed supplement and an aerosol containing the veterinary second composition containing the composition described above are also described.

A method of treating bees at or near a bee hive with a veterinary second composition is also described including administering to bees a veterinary composition described above thereby enhancing bees performance is also described.

Additional embodiments include: the method described above where said enhancing includes one or more of treating bees virus, treating bees inflammation, treating bees stress, treating bees against Colony Collapse Disorder, treating bees against *varroa*, increasing the number of bee hive brood cells, including the number of sealed brood cells, improving bees pollination activity, strengthening bees immune system and improving bees honey production.

A method of preparing the veterinary second composition described above is also described including extracting a *cannabis* plant material with an extractant to form a *cannabis* extract; and homogeneously blending said *cannabis* extract with a carrier to form said veterinary composition.

Additional embodiments include: the method described above including extracting a first *cannabis* plant material with a first extractant to form a first *cannabis* extract; extracting a second *cannabis* plant material with a second extractant to form a second *cannabis* extract; and homogeneously blending at least a fraction of said first *cannabis* extract with at least a fraction of said second *cannabis* extract and with a carrier to form said veterinary composition; the method described above where said extracting comprises contacting said *cannabis* plant material with an extractant to form a extractant-containing *cannabis* extract, removing at least a fraction of said extractant from said extractant-containing *cannabis* extract to form a desolventized *cannabis* extract and blending said desolventized *cannabis* extract with said carrier to form said veterinary composition; the method described above where said extracting comprises contacting said *cannabis* plant material with an extractant to form a extractant-containing extract, blending said extractant-containing extract with said carrier to form an extractant-containing homogeneous mixture and removing said extractant from said extractant-containing homogeneous mixture to form said veterinary composition; the method described above where said carrier comprises at least one of vegetable oil, proteins, honey, beeswax, pollen, pollen substitutes, pollen supplements nectar and/or fibers; the method described above including the homogeneous blending of said extract and said carrier with a pharmaceutical; the method described above including the homogeneous blending of said extract and said carrier with an antioxidant; the method described above including the homogeneous blending of said extract and said carrier with an emulsifier; the method described above including the homogeneous blending of said extract and said carrier with a texturizer; and the method described above including the homogeneous blending of said extract and said carrier with an extract of a plant other than a *cannabis* plant.

A description of these embodiments is included in greater detail below.

Definitions

Unless specified otherwise, all concentrations are weight concentrations and all ratios are weight per weight (weight/weight) ratios.

As used herein, the term "cannabinoid(s)" refers to both cannabinoid(s) in carboxylic acid form and cannabinoids in decarboxylated form. The same is true for each cannabinoid, e.g. THC and CBD.

As used herein, the term "non-cannabinoid *cannabis* compound" refers to a non-cannabinoid compound present in at least one strain of *cannabis* plants.

As used herein the term "terpene" refers to compounds comprising at least one isoprene unit. The terms "terpene" and "terpenoid" are used herein interchangeably.

As used herein the term "terpene other than *cannabis* terpenes" refers to a terpene that is not common to or typically doesn't exist in *cannabis* plants.

As used herein the term "flavonoid other than *cannabis* flavonoids" refers to a flavonoid that is not common to or typically doesn't exist in *cannabis* plants.

As used herein the term "extract of a non-*cannabis* plant" refers to any product of extracting a plant other than a *cannabis* plant.

As used herein, the term carrier refers to any non-*cannabis* compound.

As used herein, the term non-*cannabis* compound refers to compounds not present in *cannabis* plant or present there at concentration of less than 5%.

As used herein, the term *cannabis* plant material refers to material derived from a *cannabis* plant.

As used herein, the terms pollen, pollen substitutes and pollen supplements refer to protein-containing feed ingredients, whether containing flower pollen or not.

As used herein, the terms "honeycomb", "honeycomb frames", and "frames" are interchangeable.

As used herein, the terms administering a composition to bees refers to dispensing or applying the composition in a way that makes the composition available to bees, to bees brood and/or to bees pathogens.

As used herein, invert sugar and inverted sugar refer to the product of sucrose hydrolysis (into glucose and fructose) e.g. the result of treating sucrose with the enzyme invertase.

As used herein the term honey refers to concentrated sugar compositions referred to commercially as honey and excludes *cannabis* extract as such. As used herein, the term a comprising honey refers to comprising components of commercial pure honey (sugars, amino acids, organic acids, furfurals, vitamins, minerals).

As used herein, the term commercial pure honey refers to unadulterated honey sold globally at a rate of at least one ton per year.

As used herein, the term excipient refers to a compound used to formulate an active ingredient.

DETAILED DESCRIPTION OF THE INVENTION

Provided is a method of treating bees at or near a bee hive with a veterinary first composition comprising administering to bees a veterinary composition comprising at least one cannabinoid, and/or, at least two non-cannabinoid *cannabis* compounds, thereby enhancing bees performance.

Any form of administering and any combination of the veterinary composition with other ingredients are suitable. According to an embodiment, treating comprises administering, dispensing or supplying said veterinary composition to the bees in combination with bees feed, or with bees feed additives or with both. As use herein, the term in combination with refers to incorporated in, blended with or administering concurrently with.

For example, in many cases, bees keepers feed the bees sugar solution as an energy source during the time when nectar supply is insufficient to support the activity, e.g. before spring starts. Typically, the solutions are of 50-60% sugar and contain, sucrose, glucose, fructose, high-fructose corn syrup, inverted sugar or combinations thereof. According to an embodiment, the veterinary composition is blended with the sugar solution before feeding it to the bees or during feeding. According to an embodiment, said veterinary composition is administered in combination with each one of the sugar feeding. According to an embodiment, said veterinary composition is administered in combination with each one of the sugar feeding, whereby the veterinary composition is evenly consumed and/or evenly enhancing performance in the bee hive.

Alternatively, or additionally bees keepers feed bees with a protein ingredient, such as pollen, pollen substitutes, pollen supplements. According to an embodiment, the veterinary composition is blended with the protein ingredient before feeding it to the bees or during feeding. Any source of pollen is suitable, including *cannabis* pollen. According to an embodiment, said veterinary composition is administered in combination with each one of the protein feeding. According to an embodiment, said veterinary composition is administered in combination with each one of the protein feeding, whereby the veterinary composition is evenly consumed and/or evenly enhancing performance in the bee hive.

According to an embodiment, administering the veterinary composition comprises vaporizing the composition in the beehive, spraying the composition into the atmosphere of the beehive, spraying the composition on honeycombs in the beehive, spraying the composition on brood-containing honeycombs, incorporating the composition into beeswax used to form the beehive frames or combination thereof.

The boiling points of cannabinoids and of non-cannabinoid *cannabis* compounds, such as terpenes, typically range between about 100° C. and about 200° C. Heating to this temperature range (or to a lower temperature at sub-atmospheric pressure and/or on using a carrier gas) leads to the formation of suitable vapors to be administered to the bees. Vaporizers similar to those used for administering medical *cannabis* to patients can be used to form such vapors.

According to an embodiment, said veterinary composition is administered to the bees between 2 and 12 times per year, between 2 and 10, between 3 and 9, between 3 and 8 or between 3 and 6. According to an embodiment, said veterinary composition is administered to the bees during winter, during spring or within several weeks (e.g. within 4-6 weeks) before blooming start is predicted. According to an embodiment, said veterinary composition is administered to the bees during shortage in food, during times of negative energy balance in the hive (more energy is used than provided) during high pathogens content, during times when ambient temperature is lower than 25° C., lower than 20° C. lower than 15° C., or lower than 10° C. or during times when ambient temperature is higher than 35° C.

According to an embodiment, treating comprises administering to the bees between 1 milligram (mg) and 1000 milligram veterinary composition per beehive, between 1.5 mg and 400 mg, between 2 mg and 300 mg or between 2.5 mg and 200 mg. According to an embodiment, treating comprises administering to the bees between 0.1 mg and 300 mg cannabinoid per bee hive, between 0.2 mg and 200 mg, between 0.3 mg and 150 mg or between 0.5 mg and 100 mg. According to an embodiment, treating comprises administering to the bees between 0.1 mg and 300 mg non-cannabinoid *cannabis* compounds per bee hive, between 0.2 mg and 200 mg, between 0.3 mg and 150 mg or between 0.5 mg and 100 mg.

According to an embodiment, said veterinary composition comprises at least two cannabinoids, at least three, at least four or at least five. According to an embodiment, said veterinary composition comprises at least three non-cannabinoid *cannabis* compounds, at least four, at least five, at least six or at least ten.

According to an embodiment, said cannabinoid is selected from the group consisting of Tetrahydrocannabinol (THC), Cannabidiol (CBD), Cannabigerol (CBG), Cannabichromene (CBC), Cannabinol (CBN), Cannabielsoin (CBE), iso-Tetrahydrocannabimol (iso-THC), Cannabicyclol (CBL), Cannabicitran (CBT), Cannabivarin (CBV), Tetrahydrocannabivarin (THCV), Cannabidivarin (CBDV), Cannabichromevarin (CBCV), Cannabigerovarin (CBGV) and Cannabigerol Monomethyl Ether (CBGM), derivatives thereof and mixtures thereof.

According to an embodiment, at least one of said non-cannabinoid *cannabis* compounds is selected from the group consisting of terpenes, flavonoids, alkaloids, carotenoids and compositions thereof. According to an embodiment, at least one of said non-cannabinoid *cannabis* compounds is selected from the group consisting of pinenes, limonene, linalool, caryophyllene, myrcene, humulene, borneol, eucalyptol, terpineol and combinations thereof.

According to various embodiments, said veterinary composition comprises tetrahydrocannabinol (THC), cannabidiol (CBD) or both. According to various embodiment, said veterinary composition comprises both THC and CBD at a weight/weigh ratio between 30:1 and 1:30, between 20:1 and 1:20, or between 10:1 and 1:10.

According to an embodiment, said veterinary composition includes at least one terpene, at least two, at least three non-cannabinoid *cannabis* compounds, at least four, at least five, at least six or at least ten. According to an embodiment, said veterinary composition includes at least one flavonoid, at least two, at least three non-cannabinoid *cannabis* compounds, at least four or at least five.

According to an embodiment, said non-cannabinoid *cannabis* compounds comprise non-cannabinoid *cannabis* compounds characteristic to *Sativa cannabis* strains and/or to *Indica* strains. According to an embodiment, said non-cannabinoid *cannabis* compounds comprise non-cannabinoid *cannabis* compounds characteristic to *Sativa cannabis* strains. According to an embodiment, said non-cannabinoid *cannabis* compounds comprise non-cannabinoid *cannabis* compounds characteristic to *Indica cannabis* strains. By characteristic to such strains recited is meant that the compounds are typically contained in each of the strains recited in an amount serving to identify it as associated with such strain, but not exclusively contained in such strain, i.e., may also be present in other of the strains as well.

According to an embodiment, said veterinary composition comprises an extract of *cannabis* plant material, e.g. as formed in contacting said plant material with an extractant, and/or as formed by distilling components out of said plant material, e.g. as in steam distillation. Any extractant is suitable. According to an embodiment, said extractant is ethanol, a hydrocarbon, carbon dioxide or a combination thereof.

According to an embodiment, said veterinary composition additionally contains an emulsifier and/or an antioxidant. According to an embodiment, said veterinary composition, further comprises a compound selected from the group consisting of mono-glycerides, diglycerides, lecithin, gums (e.g. xanthan gum) and polysaccharides. According to an embodiment, said veterinary composition is lipophilic in nature and is administered in a blend with an aqueous solution and said emulsifier is selected to enable homogeneous dispersion of the veterinary composition in said aqueous solution. According to an embodiment, said emulsifier is food approved, biological and/or natural. Optionally, said veterinary composition comprises an antioxidant, whereby said veterinary composition is better protected during prolonged storage.

According to an embodiment, said veterinary composition additionally contains an additive selected from the group consisting of sugars, pollen, pollen substitutes, pollen supplements, polyunsaturated fatty acids, omega-3 fatty acids from various sources, vegetable oil (e.g. coconut oil), minerals, vitamins, fats, essential oils, naringin, beeswax, invertase enzyme and combinations thereof. According to an embodiment, said veterinary composition additionally contains a pharmaceutical. According to an embodiment, said pharmaceutical comprises antibiotics. According to an embodiment, said pharmaceutical is selected from oxytetracyline and dabicycline.

According to an embodiment, the content of said at least one cannabinoid and/or the content of said at least two non-cannabinoid *cannabis* compounds, reduces the required amount of pharmaceutical compared with veterinary compositions containing the same pharmaceutical, but without inclusion of any cannabinoids. According to an embodiment, said veterinary composition administrated to bees comprise antibiotics at an amount of less than 60 mg per beehive, less than 50 mg, less than 40 mg, less than 30 mg or less than 20 mg.

According to an embodiment, said veterinary composition additionally contains an additive selected from the group consisting of compounds characteristic to *eucalyptus* flowers, compounds characteristic to avocado flowers, compounds characteristic to orange blossom, compounds characteristic to wild flowers, characteristic to *Tribulus terrestris* and combinations thereof. By characteristic to such flowers and materials recited is meant that the compounds are typically contained in each of the flowers and materials recited in an amount serving to identify it as associated with such flower or material, but not exclusively contained in such material, i.e., may also be present in other of the flowers and materials recited as well.

According to an embodiment, said enhancing bees performance includes one or more of treating bees virus, treating bees inflammation, treating bees stress, treating bees against Colony Collapse Disorder (CCD), treating bees against *Varroa*, increasing the number of bee hive brood cells, increasing the number of bee hive sealed brood cells, improving bees pollination activity, strengthening bees immune system and improving bees honey production.

According to an embodiment, said method of treating bees at or near a bee hive, comprises administering to bees said veterinary composition, thereby reducing *Varroa* count. According to an embodiment, said method of treating bees at or near a bee hive, comprises administering to bees said veterinary composition, thereby reducing *Nosema* count. According to an embodiment, said method of treating bees at or near a bee hive, comprises administering to bees said veterinary composition, thereby reducing CCD. According to an embodiment, said method of treating bees at or near a bee hive, comprises administering to bees said veterinary composition, thereby increasing bees body size. According to an embodiment, said method of treating bees at or near a bee hive, comprises administering to bees said veterinary composition, thereby increasing honey production. According to an embodiment, said method of treating bees at or near a bee hive, comprises administering to bees said veterinary composition, thereby increasing the number of brood cells, the number of sealed brood cells, or both. According to an embodiment, said method of treating bees at or near a bee hive, comprises administering to bees said veterinary composition, thereby increasing nectar collection, increasing pollen collection, or both.

The inventors have found that administering to bees at or near a bee hive said veterinary composition enhances bees performance, e.g. as demonstrated by increased honey production, increased number of brood cells, larger bees, and accelerated movement of bees out of the hive and into it. Without wishing to be limited to a theory, such enhanced performance may result from direct effects on the bees, e.g.: increasing their need for sugars, which leads to increasing nectar collection activity; improving their health, improving their immune system and/or reducing their stress, which provides for better protection from pathogens; increasing the amount of laid eggs, which adds brood cells and increases thereby the need for pollen collection; etc. Alternatively or additionally, such enhanced performance may result from direct effects on bees pathogens, e.g. viruses, *Varroa. Nosema,* bacteria associated with brood diseases, etc. According to this alternative, administering said veterinary composition to the bees could also be understood to include administering it to bees pathogens.

According to an embodiment, the count of brood cells in said beehive, the count of sealed brood cells in said bee hive or both, is at least 10% greater than that in a bee hive under the same conditions receiving no veterinary composition treatment, at least 20% greater, at least 30% greater, at least 40% greater, at least 50% greater, at least 60% greater, at least 80% greater, at least 100% greater or at least 150% greater.

According to an embodiment, the average size of said bees is at least 10% greater than that in a bee hive under the same conditions receiving no veterinary composition treatment, at least 20% greater, at least 30% greater, at least 40% greater, at least 50% greater, at least 60% greater, at least 80% greater, or at least 100% greater.

According to an embodiment, the bees contain *Varroa* and the average *Varroa* count is at least 10% lower than that in a bee hive under the same conditions receiving no veterinary composition treatment, at least 20% greater, at least 30% greater, at least 40% greater, at least 50% greater, at least 60% greater, at least 80% greater, or at least 100% greater.

According to an embodiment, the bees contain *Nosema* and the average *Nosema* count is at least 10% lower than that in a bee hive under the same conditions receiving no veterinary composition treatment, at least 20% greater, at least 30% greater, at least 40% greater, at least 50% greater, at least 60% greater, at least 80% greater, or at least 100% greater.

According to an embodiment, the range of pollination of said bees, is greater by at least 5%, compared with bees under the same conditions receiving no veterinary composition treatment, at least 10%, at least 20%, at least 40%, at least 60%, at least 80%, at least 100%, or at least 150%. As use herein, range of pollination refers to the distance of the pollinated flowers from the treated bee hive.

According to an embodiment, the amount of pollen collected by said bees, is greater by at least 5%, compared with bees under the same conditions receiving no veterinary composition treatment, at least 10%, at least 20%, at least 40%, at least 60%, at least 80%, at least 100%, or at least 150%.

According to an embodiment, the amount of honey produced is at least 10% greater than that in a bee hive under the same conditions receiving no veterinary composition treatment, at least 20% greater, at least 30% greater, at least 40% greater, at least 50% greater, at least 60% greater, at least 80% greater, or at least 100% greater.

According to another embodiment, provided is a veterinary second composition particularly adapted for treatment of bees comprising, at least one cannabinoid and/or at least two non-cannabinoid *cannabis* compounds; a carrier; and optionally water wherein (a) said at least one cannabinoid and/or said at least two non-cannabinoid *cannabis* compounds are homogeneously dispersed in said carrier; (b) the composition includes a cannabinoid and the weight ratio between said carrier and said cannabinoid is greater than 5; (c) the composition includes a cannabinoid and water and the weight ratio between the water and said cannabinoid is greater than 5; and/or (d) the composition includes water and the weight ratio between said carrier and the water is greater than 0.5. According to various embodiments, in said composition, at least two of (a), (b), (c) or (d) are present; at least three of (a), (b), (c) or (d) are present; or all four of (a), (b), (c) and (d) are present.

According to an embodiment, said veterinary second composition comprises at least two cannabinoids, at least three, at least four or at least five. According to an embodiment, said veterinary second composition comprises at least three non-cannabinoid *cannabis* compounds, at least four, at least five, at least six or at least ten.

According to an embodiment, said cannabinoid is selected from the group consisting of Tetrahydrocannabinol (THC), Cannabidiol (CBD), Cannabigerol (CBG), Cannabichromene (CBC), Cannabinol (CBN), Cannabielsoin (CBE), iso-Tetrahydrocannabimol (iso-THC), Cannabicyclol (CBL), Cannabicitran (CBT), Cannabivarin (CBV), Tetrahydrocannabivarin (THCV), Cannabidivarin (CBDV), Cannabichromevarin (CBCV), Cannabigerovarin (CBGV) and Cannabigerol Monomethyl Ether (CBGM), derivatives thereof and mixtures thereof.

According to an embodiment, at least one of said non-cannabinoid *cannabis* compounds is selected from the group consisting of terpenes, flavonoids, alkaloids, carotenoids and compositions thereof. According to an embodiment, at least one of said non-cannabinoid *cannabis* compounds is selected from the group consisting of pinenes, limonene, linalool, caryophyllene, myrcene, humulene, borneol, eucalyptol, terpineol and combinations thereof.

According to various embodiments, said veterinary second composition comprises tetrahydrocannabinol (THC), cannabidiol (CBD) or both. According to various embodiment, said veterinary second composition comprises both THC and CBD at a weight/weigh ratio between 30:1 and 1:30, between 20:1 and 1:20, or between 10:1 and 1:10.

According to an embodiment, said veterinary second composition includes at least one terpene, at least two, at least three non-cannabinoid *cannabis* compounds, at least four, at least five, at least six or at least ten. According to an embodiment, said veterinary second composition includes at least one flavonoid, at least two, at least three non-cannabinoid *cannabis* compounds, at least four or at least five.

According to an embodiment, said non-cannabinoid *cannabis* compounds comprise non-cannabinoid *cannabis* compounds characteristic to Sativa *cannabis* strains and/or to Indica *cannabis* strains. According to an embodiment, said non-cannabinoid *cannabis* compounds comprise non-cannabinoid *cannabis* compounds characteristic to Sativa *cannabis* strains.

According to an embodiment, said non-cannabinoid *cannabis* compounds comprise non-cannabinoid *cannabis* compounds characteristic to Indica *cannabis* strains. By characteristic to such strains recited is meant that the compounds are typically contained in each of the strains recited in an amount serving to identify it as associated with such strain, but not exclusively contained in such strain, i.e., may also be present in other of the strains as well.

According to an embodiment, said veterinary second composition comprises at least one extract of *cannabis* plant material, e.g. as formed in contacting said plant material with an extractant, and/or as formed by distilling components out of said plant material, e.g. as in steam distillation. Any extractant is suitable. According to an embodiment, said extractant is ethanol, a hydrocarbon, carbon dioxide or a combination thereof.

According to an embodiment, said carrier comprises at least one of a sugar, honey, beeswax, pollen, pollen substitutes, pollen supplements, a protein ingredient, vegetable oil and fiber. According to an embodiment, said carrier comprises a sugar selected from the group consisting of sucrose, glucose, fructose, high fructose corn syrup, invert sugar and combinations thereof. According to an embodiment, said carrier comprises honey. According to an embodiment, said carrier comprises sugar and honey.

According to an embodiment, said carrier comprises an aqueous solution of at least one sugar. According to an embodiment, said carrier comprises an aqueous solution of glucose and fructose. According to an embodiment, said carrier comprises an aqueous solution of inverted sugar. According to an embodiment, sugars concentration in said aqueous solution is in the range between 20% and 80, between 30% and 70% or between 45% and 65%.

According to an embodiment, said carrier comprises solid sugar. According to an embodiment, said carrier comprises solid sugar powder. According to an embodiment, said carrier comprises a protein preparation or protein-containing plant material. According to an embodiment, said carrier comprises a mixture of pollen and sugar.

According to an embodiment, said veterinary second composition is characterized by being homogenous or of consistent composition. According to an embodiment, said at least one cannabinoid is homogeneously dispersed in said carrier. As used herein, homogeneously dispersed means consistently distributed. According to an embodiment, at least two samples of at least about 500 mg each, taken from said veterinary second composition have similar concentrations of said at least one cannabinoid, e.g. within 10% difference. According to an embodiment, at least two samples of at least about 500 mg each, taken from said veterinary second composition comprising multiple cannabinoids, have similar concentrations of multiple (e.g. at least 2, at least 3, at least 5 or at least 10) cannabinoid, e.g. within 10% difference (e.g. in case said therapeutic composition comprises cannabinoid A and cannabinoid B, the concentration of cannabinoid A in one sample is similar to the concentration of cannabinoid A in another sample and the concentration of cannabinoid B in one sample is similar to the concentration of cannabinoid B in another sample).

According to an embodiment, said at least two non-cannabinoid *cannabis* compounds are homogeneously dispersed in said carrier. According to an embodiment, at least two samples of at least about 500 mg each, taken from said veterinary second composition have similar concentrations of said at least two non-cannabinoid *cannabis* compounds, e.g. within 10% difference.

According to an embodiment, said veterinary second composition includes a cannabinoid and the weight ratio between said carrier and said cannabinoid is greater than 5, greater than 8, greater than 15, greater than 20, greater than 25, greater than 30, greater than 40, greater than 50, greater than 60, or greater than 80. According to an embodiment, said veterinary second composition includes non-cannabinoid *cannabis* compounds and the weight ratio between said carrier and said non-cannabinoid *cannabis* compounds is greater than 5, greater than 8, greater than 15, greater than 20, greater than 25, greater than 30, greater than 40, greater than 50, greater than 60, or greater than 80.

According to an embodiment, said veterinary second composition comprises at least 0.001% by weight cannabinoid, at least 0.001% by weight non-cannabinoid *cannabis* compounds and at least 40% by weight carrier. According to an embodiment, it comprises at least 0.001% by weight cannabinoid, at least 0.002%, at least 0.004%, at least 0.006%, at least 0.008%, at least 0.01%, at least 0.02%, at least 0.03%, at least 0.04%, at least 0.06%, at least 0.08%, at least 0.1%, at least 0.2%, at least 0.4%, at least 0.6%, at least 0.8% or at least 1%. According to an embodiment, it comprises less than 10% by weight cannabinoid, less than 8%, less than 6%, less than 4%, less than 2%, less than 1%, less than 0.8% or less than 0.5%. According to an embodiment, said veterinary second composition comprises at least 0.001% by weight non-cannabinoid *cannabis* compounds, at least 0.002%, at least 0.004%, at least 0.006%, at least 0.008%, at least 0.01%, at least 0.02%, at least 0.03%, at least 0.04%, at least 0.06%, at least 0.08%, at least 0.1%, at least 0.2%, at least 0.4%, at least 0.6%, at least 0.8% or at least 1%. According to an embodiment, it comprises less than 10% by weight non-cannabinoid *cannabis* compounds, less than 8%, less than 6%, less than 4%, less than 2%, less than 1%, less than 0.8% or less than 0.5%. According to an embodiment, said veterinary second composition comprises at least 45% by weight carrier, at least 50%, at least 55%, at least 60%, at least 65%, at least 70%, at least 75%, at least 80% or at least 85%.

According to an embodiment, said veterinary second composition includes a cannabinoid and water and the weight ratio between the water and said cannabinoid is greater than 5, greater than 8, greater than 15, greater than 20, greater than 25, greater than 30, greater than 40, greater than 50, greater than 60, or greater than 80.

According to an embodiment, said veterinary second composition includes non-cannabinoid *cannabis* compounds and water and the weight ratio between the water and said non-cannabinoid *cannabis* compounds is greater than 5, greater than 8, greater than 15, greater than 20, greater than 25, greater than 30, greater than 40, greater than 50, greater than 60, or greater than 80.

According to various embodiments, said veterinary second composition comprises at least one cannabinoid and/or at least two non-cannabinoid *cannabis* compounds, at least 40% by weight sugar and at least 40% by weight water; at least one cannabinoid, at least 40% by weight sugar and at least 40% by weight water; at least two non-cannabinoid *cannabis* compounds, at least 40% by weight sugar and at least 40% by weight water; or at least one cannabinoid, at least two non-cannabinoid *cannabis* compounds, at least 40% by weight sugar and at least 40% by weight water.

According to various embodiments, in said veterinary second composition said at least one cannabinoid and/or said at least two non-cannabinoid *cannabis* compounds are homogeneously dispersed in said carrier; said at least one cannabinoid is homogeneously dispersed in said carrier; said at least two non-cannabinoid *cannabis* compounds are homogeneously dispersed in said carrier; or said at least one cannabinoid and said at least two non-cannabinoid *cannabis* compounds are homogeneously dispersed in said carrier.

According to an embodiments, said veterinary second composition comprises at least one cannabinoid and/or at least two non-cannabinoid *cannabis* compounds and additionally containing pollen, pollen substitutes and/or pollen supplements. Any source of pollen is suitable, including *cannabis* pollen. According to an embodiments, said veterinary second composition includes at least one cannabinoid and/or at least two non-cannabinoid *cannabis* compounds and additionally contains 30% protein.

According to an embodiment, said veterinary second composition additionally contains an emulsifier and/or an antioxidant. According to an embodiment, said emulsifier is food approved, biological and/or natural. According to an embodiment, said veterinary second composition, further comprises a compound selected from the group consisting of mono-glycerides, diglycerides, lecithin, gums (e.g. xanthan gum) and polysaccharides. Optionally, said veterinary second composition comprises an antioxidant, whereby said veterinary second composition is better protected during prolonged storage.

According to an embodiment, said veterinary second composition additionally contains an additive selected from the group consisting of sugars, pollen, pollen substitutes, pollen supplements, omega-polyunsaturated fatty acids, 3 fatty acids from various sources, vegetable oil (e.g. coconut oil), minerals, vitamins, fats, essential oils, beeswax, naringin, invertase enzyme, and combinations thereof. According to an embodiment, said veterinary second composition additionally contains a pharmaceutical. According to an embodiment, said pharmaceutical comprises antibiotics. According to an embodiment, said pharmaceutical is selected from oxytetracyline and dabicycline.

According to an embodiment, said veterinary second composition additionally contains an additive, e.g. a terpene, selected from the group consisting of compounds characteristic to *eucalyptus* flowers, compounds characteristic to avocado flowers, compounds characteristic to orange blossom, compounds characteristic to wild flowers, characteristic to *Tribulus terrestris* and combinations thereof. By characteristic to such flowers and materials recited is meant that the compounds are typically contained in each of the flowers and materials recited in an amount serving to identify it as associated with such flower or material, but not exclusively contained in such material, i.e., may also be present in other of the flowers and materials recited as well.

According to an embodiment, said veterinary second composition, further comprises at least 10 ppm terpene other than *cannabis* terpenes, at least 50 ppm, at least 100 ppm, at least 500 ppm, at least 1000 ppm, at least 3000 ppm, at least 5000 ppm or at least 10000 ppm.

According to an embodiment, said veterinary second composition, further comprises at least one excipient. According to an embodiment, said excipient is said carrier.

According to an embodiment, said at least one cannabinoid and at least two non-cannabinoid *cannabis* compounds are homogeneously dispersed in said carrier and said veterinary second composition comprises said homogeneous dispersion and at least one excipient. According to an embodiment, said excipient coats said homogeneous dispersion.

According to an embodiment, said veterinary second composition is in solid form, in liquid form, in aerosol form, in gel form, in tablet form or in a capsule form. According to an embodiment, further provided is an aerosol comprising said veterinary second composition. According to an embodiment, further provided is a solid preparation comprising said veterinary second composition. According to an embodiment, further provided is a liquid preparation comprising said veterinary second composition.

According to an embodiment, further provided is a bee feed supplement containing said veterinary second composition.

According to an embodiment, further provided is bee veterinary medication comprising said veterinary second composition.

According to an embodiment, further provided is a method of treating bees at or near a bee hive with a veterinary second composition comprising administering to bees a said veterinary second composition thereby enhancing bees performance. According to an embodiment, said enhancing includes one or more of treating bees virus, treating bees inflammation, treating bees stress, treating bees against Colony Collapse Disorder, treating bees against *Varroa*, increasing the number of bee hive brood cells, increasing the number of bee hive sealed brood cells, improving bees pollination activity, strengthening bees immune system and improving bees honey production.

According to an embodiment, said method of treating bees at or near a bee hive, comprises administering to bees said veterinary second composition, thereby reducing *Varroa* count. According to an embodiment, said method of treating bees at or near a bee hive, comprises administering to bees said veterinary second composition, thereby reducing *Nosema* count. According to an embodiment, said method of treating bees at or near a bee hive, comprises administering to bees said veterinary second composition, thereby reducing CCD. According to an embodiment, said method of treating bees at or near a bee hive, comprises administering to bees said veterinary second composition, thereby increasing bees body size. According to an embodiment, said method of treating bees at or near a bee hive, comprises administering to bees said veterinary second composition, thereby increasing honey production. According to an embodiment, said method of treating bees at or near a bee hive, comprises administering to bees said veterinary second composition, thereby increasing the number of brood cells, the number of sealed brood cells, or both. According to an embodiment, said method of treating bees at or near a bee hive, comprises administering to bees said veterinary second composition, thereby increasing nectar collection, increasing pollen collection, or both.

The inventors have found that administering to bees at or near a bee hive said veterinary second composition enhances bees performance, e.g. as demonstrated by increased honey production, increased number of brood cells, larger bees, and accelerated movement of bees out of the hive and into it. Without wishing to be limited to a theory, such enhanced performance may result from direct effects on the bees, e.g.: increasing their need for sugars, which leads to increasing nectar collection activity; improving their health, improving their immune system and/or reducing their stress, which provides for better protection from pathogens; increasing the number of laid eggs, which adds brood cells and increases thereby the need for pollen collection; etc. Alternatively or additionally, such enhanced performance may result from direct effects on bees pathogens, e.g. viruses, *Varroa*, *Nosema*, bacteria associated with brood diseases, etc. According to this alternative, administering said veterinary second composition to the bees could result in administering the composition to bees pathogens.

According to an embodiment, the count of brood cells in said beehive, the count of sealed brood cells in said bee hive or both, is at least 10% greater than that in a bee hive under the same conditions receiving no veterinary composition treatment, at least 20% greater, at least 30% greater, at least 40% greater, at least 50% greater, at least 60% greater, at least 80% greater, at least 100% greater or at least 150% greater.

According to an embodiment, the average size of said bees is at least 10% greater than that in a bee hive under the same conditions receiving no veterinary composition treatment, at least 20% greater, at least 30% greater, at least 40% greater, at least 50% greater, at least 60% greater, at least 80% greater, or at least 100% greater.

According to an embodiment, the bees contain *Varroa* and the average *Varroa* count is at least 10% lower than that in a bee hive under the same conditions receiving no veterinary composition treatment, at least 20% greater, at least 30% greater, at least 40% greater, at least 50% greater, at least 60% greater, at least 80% greater, or at least 100% greater.

According to an embodiment, the bees contain *Nosema* and the average *Nosema* count is at least 10% lower than that in a bee hive under the same conditions receiving no veterinary composition treatment, at least 20% greater, at least 30% greater, at least 40% greater, at least 50% greater, at least 60% greater, at least 80% greater, or at least 100% greater.

According to an embodiment, the amount of honey produced is at least 10% greater than that in a bee hive under the same conditions receiving no veterinary composition treatment, at least 20% greater, at least 30% greater, at least 40% greater, at least 50% greater, at least 60% greater, at least 80% greater, or at least 100% greater.

According to an embodiment, said veterinary second composition is administered to the bees between 2 and 12 times per year, between 2 and 10, between 3 and 9, between 3 and 8 or between 3 and 6. According to an embodiment, said veterinary second composition is administered to the bees during winter, during spring or within several weeks (e.g. within 4-6 weeks) before blooming start is predicted. According to an embodiment, said veterinary second composition is administered to the bees during shortage in food, during times of negative energy balance in the hive (more energy is used than provided) during high pathogens content, during times when ambient temperature is lower than 25° C., lower than 20° C. lower than 15° C., or lower than 10° C. or during times when ambient temperature is higher than 35° C.

According of an embodiment, further provided is a method of preparing said veterinary second composition, comprising extracting a *cannabis* plant material with an extractant to form a *cannabis* extract; and homogeneously blending said *cannabis* extract with a carrier to form said veterinary second composition. According to an embodiment, said extracting comprises contacting said plant material with an extractant, and/or distilling components out of said plant material, e.g. as in steam distillation. Any extractant is suitable. According to an embodiment, said extractant comprises ethanol, hydrocarbon, carbon dioxide (e.g. in a super-critical, near critical, or a sub-critical form) or carbon dioxide mixtures with other solvents, e.g. ethanol.

According to an embodiment, said method comprises extracting a first *cannabis* plant material with a first extractant to form a first *cannabis* extract; extracting a second *cannabis* plant material with a second extractant to form a second *cannabis* extract; and homogeneously blending at least a fraction of said first *cannabis* extract with at least a fraction of said second *cannabis* extract and with a carrier to form said veterinary second composition. According to an embodiment, said first extractant is similar to said second extractant, e.g. both comprise at least 60% of a given component (e.g. ethanol), at least 70%, at least 80% or at least 90%.

According to an embodiment, said method comprises extracting multiple *cannabis* plant materials (e.g. two, three, four, five or more) with extractants to form multiple *cannabis* extracts and forming said veterinary second composition by homogeneous mixing fractions of multiple extracts and said carrier. According to various embodiments, extractant is at least partially removed from at least some of the extracts prior to said mixing or simultaneously with it and most of the residual extractant is removed post said mixing.

According to an embodiment, said method further comprises keeping *cannabis* plant material prior to said extracting at conditions suitable for reducing their moisture content, e.g. in contact with low-moisture air, to form partially dried *cannabis* plant material. According to an embodiment, water content of said *cannabis* plant material is less than 20%, less than 18%, less than 16%, less than 14%, less than 12% or less than 10%. According to an embodiment, said *cannabis* plant material is kept at suitable conditions for duration long enough to reach an even distribution of the moisture.

According to an embodiment, said extracting comprises contacting said *cannabis* plant material with an extractant to form an extractant-containing *cannabis* extract, removing at least a fraction of said extractant from said extractant-containing *cannabis* extract to form a desolventized *cannabis* extract and homogeneously blending said desolventized *cannabis* extract with said carrier to form said veterinary second composition.

According to an embodiment, said extracting comprises contacting said *cannabis* plant material with an extractant to form an extractant-containing extract, optionally removing a fraction of said extractant and homogeneously blending said extractant containing extract with said carrier to form an extractant-containing homogeneous mixture and removing said extractant from said extractant-containing homogeneous mixture to form said veterinary second composition. According to an embodiment, said carrier is crystalline and/or solid (e.g. sugar, pollen or beeswax) and said blending said extractant containing extract with said carrier comprises spraying said extractant containing extract on said carrier.

According to various embodiments, said method includes homogeneous blending of said extract and said carrier with a pharmaceutical; homogeneous blending of said extract and said carrier with an antioxidant; homogeneous blending of said extract and said carrier with an emulsifier; homogeneous blending of said extract and said carrier with a texturizer; and/or homogeneous blending of said extract and said carrier with an extract of a plant other than a *cannabis* plant. Any sequence of mixing is suitable.

According to an embodiment, said method further includes homogeneously blending of said extract or extracts (extractant comprising or desolventized) and said carrier with at least two out of the group consisting of a pharmaceutical, an antioxidant, an emulsifier, a texturizer, a flavoring, naringin, polyunsaturated fatty acids, a vitamin, and an extract of a plant other than a *cannabis* plant, at least three, at least four or at least five. Any sequence of mixing is suitable.

Any form of extractant removal is suitable. According to an embodiment, extractant is removed by distillation.

According to an embodiment, said method further comprises maintaining at least one of said extractant-comprising extract, desolventized *cannabis* extract, extractant-comprising homogeneous mixture and desolventized homogeneous mixture at a temperature and for a duration sufficient for decarboxylating, at least partially, acid form of comprised cannabinoids.

EXAMPLES

Example 1

Preparing *Cannabis* Extracts

Buds of two strains were dried at ambient temperature and at controlled moisture. The dried buds were then ground and mixed well for homogenization. Moisture content was 11.2% wt. The dried and ground plant material was extracted by mixing with 95% ethanol solution at 10 milliliter (ml) ethanol solution per 1 gram of plant material. Mixing was conducted at ambient temperature for 30 minutes. Then the plant material was filtered out and the solution was evaporated at sub-atmospheric pressure for removing the majority of the ethanol. The remaining solution was kept in a freezer for at least 24 hours, followed by filtering out waxes. The de-waxed solution was further evaporated for removing the rest of the ethanol. The residual solution was then kept at a temperature of 120° C. until bubbling stopped to form the decarboxylated extract. Samples of the extracts were analyzed for their cannabinoids content. The results are summarized in Table 1:

TABLE 1

| Extract | Strain (source in Israel) | CBD (% wt) | CBN (% wt) | THC (% wt) |
|---------|---------------------------|------------|------------|------------|
| 1 | CHEESE-PIE (Better) | 61.1 | | 2.8 |
| 2 | QUARTZ (BOL) | | 1.0 | 61.3 |

Example 2

Blending Extracts with Sucrose Solutions

Food-grade sucrose was mixed with water to form an aqueous solution of 55% sucrose.
Comparative Method:
Several trials were made to form homogeneous mixtures where said 55% sucrose solution forms a carrier to deliver the extracts of Example 1. The weight/weight ratios between the extracts and the 55% sucrose solutions were selected to reach cannabinoids concentration in the mixture in the range between 20 ppm and 1000 ppm. No homogeneous solution was formed. At least a fraction of the extract remained undissolved and tended to stick to the walls of the sugar container.

Working Method:

The extract was mixed with honey to form extract-honey mixtures and those extract-honey mixtures were mixed with the 55% sucrose solution. Thus, 30-50 grams honey as such or after dilution with 10% water, 20% water or 30% water, was warmed to 45° C. Then the extract was gradually added, while thoroughly mixing. Mixing was continued for 30 minutes after the addition is completed, whereby extract-honey mixtures were formed. The 55% sucrose solution was gradually added to the extract-honey mixtures until the desired overall cannabinoid concentration was reached. The weight/weight ratio between honey and the sucrose solution were in the range between 1:10 and 1:1000. At all tested cannabinoid concentrations, up to several thousand parts per million, the formed final solutions were homogeneous.

Example 3

Production of the Veterinary Composition

The working method of Example 2 was used to prepare veterinary compositions containing 55% sucrose, honey and extract. In preparing the veterinary composition, the weight/weight ratio between honey and the sucrose solution was 1:20. Three types of veterinary composition were prepared according to Table 2.

TABLE 2

Veterinary compositions

| Veterinary composition | Source [1] | Cannabinoid concentration (ppm) | |
|---|---|---|---|
| | | THC | CBD |
| A | Extract 1 | 2 | 41 |
| B | Extract 2 | 41 | |
| C | Extract 1 + Extract 2 | 20.5 | 20.5 |

[1] Source of cannabinoids and of non-cannabinoid cannabis compounds

Example 4

Administering the Veterinary Compositions

For administering the veterinary compositions to bees at or near a bee hive, freshly prepared veterinary compositions, containing the desired amounts of cannabinoids and of non-cannabinoid *cannabis* compounds, were mixed with 55% sucrose solution to form feeds. The feeds were provided to the bees in feeding trays. The majority of the feed was consumed within several hours.

Example 5

Trial Bee Hive Setting

Eighteen bee hives were selected and randomly divided into three groups—Group 1, Group 2 and Group 3—each one containing six hives. All hives were positioned at the same location in a field at Kfar Bilu, Israel.

Example 6

Feeds for the Various Groups

The groups were fed four times during February and March 2016:

Group 1 received three feeds ($1^{st}$, $3^{rd}$ and $4^{th}$) prepared by forming veterinary compositions according to A in Example 3 and mixing them with 55% sucrose solution according to Example 4. The $2^{nd}$ feeding was prepared by forming a veterinary composition according to C in Example 3 and mixing it with 55% sucrose solution according to Example 4.

Group 2 received four feeds prepared by forming veterinary compositions according to B in Example 3 and mixing them with 55% sucrose solution according to Example 4.

Group 3 (control) received four 55% sucrose solutions.

Example 7

Feeding Schedule and Details

The feeding and their timing are summarized in Table 3.

TABLE 3

Feeding schedule and details

| | | Group 1 | Group 2 | Group 3 |
|---|---|---|---|---|
| $1^{st}$ feeding | Date | | | |
| | Feed amount per hive (Kg) (kilograms) | 3 | 3 | 3 |
| | Cannabinoid per hive | 3 mg CBD | 3 mg THC | 0 |
| | Non-cannabinoid [1] per hive | 2 mg | 2 mg | 0 |
| $2^{nd}$ feeding | Date | | | |
| | Feed amount per hive (Kg) | 3 | 3 | 3 |
| | Cannabinoid per hive | 1.5 mg CBD + 1.5 mg THC | 3 mg THC | 0 |
| | Non-cannabinoid [1] per hive | 2 mg | 2 mg | 0 |
| $3^{rd}$ feeding | Date | | | |
| | Feed amount per hive (Kg) | 3 | 3 | 3 |
| | Cannabinoid per hive | 6.7 mg CBD | 6.7 mg THC | 0 |
| | Non-cannabinoid [1] per hive | 4.4 mg | 4.4 mg | 0 |
| $4^{th}$ feeding | Date | | | |
| | Feed amount per hive (Kg) | 3 | 3 | 3 |
| | Cannabinoid per hive | 6.7 mg CBD | 6.7 mg THC | 0 |
| | Non-cannabinoid [1] per hive | 4.4 mg | 4.4 mg | 0 |

[1] Non-cannabinoid cannabis composition

Example 8

Number of Full Honeycombs

At various dates, all hives were checked for the number of full honeycombs therein. Table 4 summarizes the average number of full honeycombs per hive at the checking dates.

TABLE 4

Average number of full honeycombs per hive

| Date | Full honeycombs per hive | | |
|---|---|---|---|
| | Group 1 | Group 2 | Group 3 |
| Feb. 5, 2016 | 6.2 | 5.2 | 6 |
| Feb. 16, 2016 | 8.3 | 6.4 | 7.8 |
| Mar. 6, 2016 | 9.8 | 9.2 | 9.7 |
| Mar. 14, 2016 | 14 | 15.5 | 11.3 |
| Mar. 22, 2016 | 18 | 17.4 | 11.3 |
| Apr. 5, 2016 | 22.4 | 21.2 | 14.2 |
| May 2, 2016 | 23.6 | 21.3 | 18.7 |

These number of full honeycombs per hive demonstrate 60% enhancement in performance as a result of administering few milligrams of cannabinoid and/or few milligrams of non-cannabinoid *cannabis* compounds per bee hive.

Example 9

Honey Harvest

Honey was first harvested on May 18, 2016. Second harvest was on Aug. 1, 2016. The average amounts of honey per hive are summarized in Table 5.

TABLE 5

Average amount of harvested honey per hive

| | Harvested honey per hive (Kg) | | |
|---|---|---|---|
| | Group 1 | Group 2 | Group 3 |
| 1$^{st}$ harvest | 22.7 | 18.1 | 14.8 |
| 2$^{nd}$ harvest | 16.6 | 18.9 | 12.1 |
| Total | 39.3 | 37.0 | 26.9 |

The average amount of harvested honey is another indication of improved performance on administering few milligrams of cannabinoid and/or few milligrams of non-cannabinoid *cannabis* compounds per bee hive.

Example 10

*Varroa* Count

*Varroa* count was conducted on Aug. 1, 2016. The results of average *Varroa* count per bee hive are summarized in Table 6.

TABLE 6

Average Varroa count per hive

| | Varroa count per hive | | |
|---|---|---|---|
| | Group 3 | Group 2 | Group 1 |
| Varroa count | 438 | 480 | 313 |

The invention claimed is:

1. A method of treating bees at or near a bee hive with a veterinary first composition comprising administering to the bees a therapeutically effective amount of the veterinary first composition comprising at least one cannabinoid, and/or, at least two non-cannabinoid *cannabis* compounds.

2. The method of claim 1, wherein said enhancing includes one or more of treating bees virus, treating bees inflammation, treating bees stress, treating bees against Colony Collapse Disorder, treating bees against *Varroa*, increasing the number of bee hive brood cells, including the number of bee hive sealed brood cells, improving bees pollination activity, strengthening bees immune system and improving bees honey production.

3. The method of claim 1, wherein said veterinary composition comprises an extract of *cannabis* plant material.

4. The method of claim 1, wherein said veterinary composition additionally contains an additive selected from the group consisting of emulsifiers, antioxidants, sugars, pollen, pollen substitutes, pollen supplements, omega-3 fatty acids, vegetable oil, minerals, vitamins, fats, essential oils, invertase enzyme and combinations thereof.

5. The method of claim 1, wherein said veterinary composition additionally contains an additive selected from the group consisting of an extract of *eucalyptus* flowers, an extract of avocado flowers, an extract of orange blossoms, an extract of wild flowers, an extract of *Tribulus terrestris* and combinations thereof.

6. The method of claim 1, comprising administering said veterinary composition to the bees in combination with at least one of bees feed, bees feed additives, sugars and protein ingredient.

7. The method of claim 1, wherein said administering comprises vaporizing the composition in the beehive, spraying the composition into the atmosphere of the beehive, spraying the composition on honeycombs in the beehive, spraying the composition on brood-containing honeycombs, incorporating the composition into beeswax used to form the beehive frames or combinations thereof.

8. The method of claim 1, comprising administering said veterinary composition to the bees during winter.

9. The method of claim 1, comprising administering said veterinary composition to the bees when present at or near a beehive containing brood cells, wherein the count of brood cells in said beehive, the count of sealed brood cells in said beehive or both is at least 10% greater than those in a beehive under the same conditions receiving no veterinary composition treatment.

10. The method of claim 1, wherein average size of said bees is at least 10% greater than that of bees under the same conditions receiving no veterinary composition treatment.

11. The method of claim 1, wherein the bees contain *Varroa* and the average *varroa* count in said bees is at least 10% lower than that of bees under the same conditions receiving no veterinary composition treatment.

12. The method of claim 11, wherein said enhancing includes one or more of treating bees virus, treating bees inflammation, treating bees stress, treating bees against Colony Collapse Disorder, treating bees against *varroa*, increasing the number of bee hive brood cells, including the number of sealed brood cells, improving bees pollination activity, strengthening bees immune system and improving bees honey production.

13. The method of claim 1, wherein the first composition further comprises a carrier or water, and wherein the ratio of the carrier or the water to the cannabinoid by weight is greater than 5:1.

* * * * *